(12) United States Patent
Dong

(10) Patent No.: US 7,198,638 B2
(45) Date of Patent: *Apr. 3, 2007

(54) LOW PROFILE, HIGH STRETCH, LOW DILATION KNIT PROSTHETIC DEVICE

(75) Inventor: Jerry Q. Dong, Oakland, NJ (US)

(73) Assignee: SciMed Life System, Inc., Maple Grove, MN (US)

( * ) Notice: Subject to any disclaimer, the term of this patent is extended or adjusted under 35 U.S.C. 154(b) by 427 days.

This patent is subject to a terminal disclaimer.

(21) Appl. No.: 10/323,569

(22) Filed: Dec. 19, 2002

(65) Prior Publication Data

US 2003/0125796 A1  Jul. 3, 2003

Related U.S. Application Data

(63) Continuation of application No. 09/898,103, filed on Jul. 3, 2001, now Pat. No. 6,554,855.

(51) Int. Cl.
*A61F 2/06* (2006.01)

(52) U.S. Cl. .................. 623/1.13; 623/1.5; 66/195

(58) Field of Classification Search ............... 623/1.13, 623/1.5–1.54, 1.3; 66/192–195
See application file for complete search history.

(56) References Cited

U.S. PATENT DOCUMENTS

| | | | |
|---|---|---|---|
| 3,340,134 A | 9/1967 | Porter et al. | |
| 3,474,644 A | 10/1969 | Frank | |
| 3,986,828 A * | 10/1976 | Hoffman et al. | ............ 8/115.68 |
| 4,015,451 A | 4/1977 | Gajjar | |
| 4,052,866 A | 10/1977 | Saunders | |
| 4,064,712 A | 12/1977 | Sayre et al. | |
| 4,193,137 A * | 3/1980 | Heck | ............ 623/1.52 |
| 4,307,587 A | 12/1981 | Baesgen et al. | |
| 5,407,722 A | 4/1995 | Peake, III et al. | |
| 5,449,530 A | 9/1995 | Peake, III et al. | |
| 5,456,711 A * | 10/1995 | Hudson | ............ 623/1.5 |
| 5,611,127 A | 3/1997 | Ceriani et al. | |
| 5,732,572 A * | 3/1998 | Litton | ............ 66/195 |
| 5,843,158 A | 12/1998 | Lenker et al. | |
| 6,161,399 A * | 12/2000 | Jayaraman | ............ 66/170 |
| 6,217,609 B1 | 4/2001 | Haverkost | |
| 6,287,316 B1 * | 9/2001 | Agarwal et al. | ............ 606/151 |
| 6,408,656 B1 * | 6/2002 | Ory et al. | ............ 66/195 |
| 6,540,773 B2 * | 4/2003 | Dong | ............ 623/1.13 |
| 6,547,820 B1 * | 4/2003 | Staudenmeier | ............ 623/1.49 |
| 6,554,855 B1 * | 4/2003 | Dong | ............ 623/1.13 |

FOREIGN PATENT DOCUMENTS

FR  2 714 816 A1  4/2001

* cited by examiner

*Primary Examiner*—Suzette Gherbi
(74) *Attorney, Agent, or Firm*—Hoffmann & Baron, LLP

(57) ABSTRACT

A radially expandable stent-graft endoprosthesis is provided. The graft included in the stent-graft is a knitted tubular structure circumferentially disposed and securably attached to the stent. The knitted tubular structure has a warp knit pattern of interlacing yarns with at least a two-needle underlap to provide greater than 150 percent longitudinal stretchability while substantially inhibiting dilation. A knitted tubular graft and a knitted medical fabric with greater than 150 percent longitudinal stretchability are also provided.

31 Claims, 11 Drawing Sheets

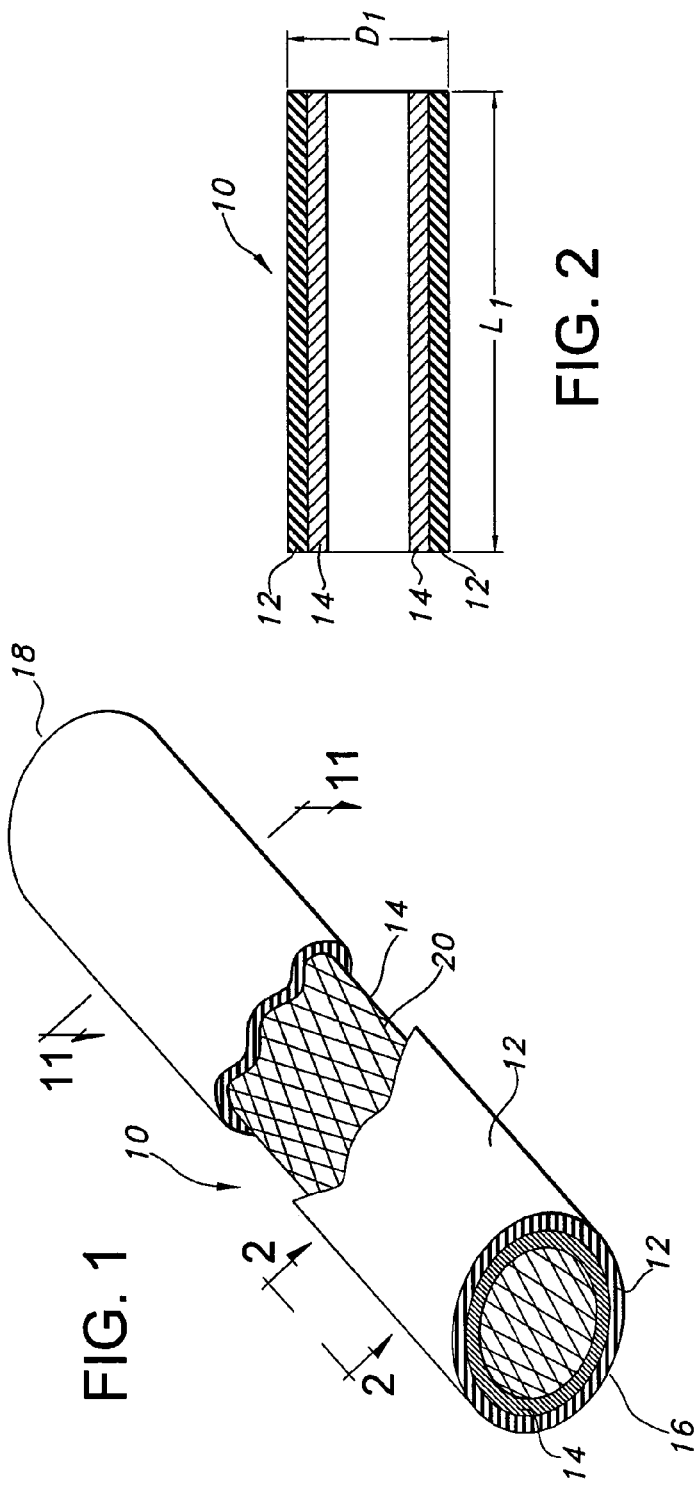

LOW PROFILE, HIGH STRETCH, LOW DILATION KNIT PROSTHETIC DEVICE

CROSS REFERENCE TO RELATED APPLICATION

This application is a continuation of U.S. application Ser. No. 09/898,103, filed Jul. 3, 2001, now U.S Pat. No. 6,554,855, the contents of which are incorporated herein by reference.

FIELD OF INVENTION

The present invention relates generally to a tubular implantable prosthesis having a knitted textile structure. More particularly, the present invention relates to an endoprosthesis with a knitted textile structure having increased longitudinal stretchability and further having radially restricted enlargement.

BACKGROUND OF RELATED TECHNOLOGY

An intraluminal prosthesis is a medical device used in the treatment of diseased blood vessels. An intraluminal prosthesis is typically used to repair, replace, or otherwise correct a diseased or damaged blood vessel. An artery or vein may be diseased in a variety of different ways. The prosthesis may therefore be used to prevent or treat a wide variety of defects such as stenosis of the vessel, thrombosis, occlusion or an aneurysm.

One type of intraluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures and aneurysms in various blood vessels. These devices are implanted within the vessel to open and/or reinforce collapsing or partially occluded sections of the vessel.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern. Examples of various stent configurations are shown in U.S. Pat. No. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten and U.S. Pat. No. 4,886,062 to Wiktor, all of whose contents are incorporated herein by reference.

A graft is another commonly known type of intraluminal prosthesis which is used to repair and replace various body vessels. A graft provides a lumen through which blood may flow. Moreover, a graft is often configured to have porosity to permit the ingrowth of cells for stabilization of an implanted graft while also being generally impermeable to blood to inhibit substantial leakage of blood therethrough. Grafts are typically tubular devices which may be formed of a variety of materials, including textile and non-textile materials.

A stent and a graft may combined into a stent-graft endoprosthesis to combine the features thereof. The graft, however, in the stent-graft endoprosthesis should comply with the implantation requirements of the stent which often include collapsing the stent for placement at an implantation site and expansion of the stent for securement thereat. Grafts which cannot easily accommodate the longitudinal and/or radial dimensional changes from a unexpanded or collapsed state to an expanded stent often complicate the implantation of the stent-graft. For instance, some grafts are folded in the collapsed or unexpanded state and must be subsequently be unfolded to accommodate the expanded stent. The unfolding of the graft, however, often complicates the placement of the graft on the stent and the implantation of the stent-graft itself. Alternatively, noncontiguous grafts have been used with expandable stent-grafts. Upon expansion of the stent, however, portions of the noncontiguous graft often separate to accommodate the stent expansion. This separation leaves gaps in the graft structure thereby permitting the leakage of blood through these gaps.

Moreover, an intraluminal device, such as a stent, a graft or a stent-graft, may dilate over time after implantation within a bodily lumen. The dilation of the implanted intraluminal device is a radial enlargement of the device resulting from pulsating stresses or pressures present within the bodily lumen. The action of the pulsating stresses or pressures often fatigue the structure of the device resulting in radial expansion and possibly longitudinal foreshortening.

A variety of mechanical means have been used to attempt to limit device dilation. For example, U.S. Pat. No. 5,843,158 to Lenker et al. describes the use of generally inelastic frame rings circumferentially disposed along a radially contractible stent-graft. The frames are described as limiting the radial expansion. Such frames, however, must be integral to the stent and complicate the stent-graft geometry.

U.S. Pat. No. 5,843,158 to Lenker et al. further describes mechanical means for limiting radial expansion of a graft in a stent-graft. In one alternative, the stent graft includes an internal liner. The internal liner is described as an inelastic material and is folded within the stent graft. Upon radial expansion of stent-graft, the internal liner is described as further limiting the radial expansion of the stent-graft. Furthermore, a graft containing circumferential composite yarns is described as yet another alternative for limiting radial expansion. The composite yarns are described as having inexpansible yarns counter wound or braided over an elastic core yarn. The inexpansive yarns are described as limiting radial expansion of graft. These attempts to limit radial expansion of a stent-graft, however, result in complicated the stent-graft designs that have either additional liners or complex composite yarn designs.

Thus, there is a need for a graft that compliments the implantation of an expandable stent of a stent-graft endoprosthesis and limits dilation without the disadvantages of the prior art. In particular, there is need for a graft that is securably attached to the stent in both the expanded and unexpanded state which limits without complicating the mechanical dynamics of the stent or the graft.

SUMMARY OF THE INVENTION

The present invention provides an implantable tubular prosthesis having a radially expandable tubular stent structure having a first diameter and capable of longitudinal expansion or contraction to achieve a second diameter which is different from the first diameter and a tubular knitted tubular graft circumferentially disposed and securably attached to the stent. The graft has a pattern of interlaced wale and course yarns in a warp knit pattern to permit longitudinal expansion or contraction of the graft substantially consistent with the longitudinal expansion or contraction of the stent.

The prosthesis of the present invention is capable of longitudinal expansion from 50 to 200 percent by length from a quiescent state. Alternatively, the prosthesis of the present invention is capable of 50 to 200 percent longitudinal contraction by length to achieve a substantially quiescent state from an unexpanded state. Furthermore, the textile graft of the present invention is substantially fluid-tight in its quiescent state.

To achieve such a degree of longitudinal expansion or contraction the textile graft includes a single layer, warp knit pattern having a set yarns diagonally shifted over two or more yarns before forming a loop between engaging yarns. The knit pattern is generally described as a warp knit pattern with at least a two needle underlap. Such patterns depart a high degree of flexibility and stretchability to the textile graft of the present invention. Moreover, such patterns substantially inhibits radial expansion of the textile graft beyond a desired diameter to limit dilation of the graft.

In one aspect of the present invention an implantable tubular prosthesis is provided which is capable of longitudinal expansion from a quiescent state to an elongated state including a radially contractible and longitudinally expandable tubular stent having a quiescent diameter and quiescent length capable of longitudinal expansion to the elongated state having an elongated length and a contracted diameter, wherein the elongated length is greater than the quiescent length and the contracted diameter is smaller than the quiescent diameter. The prosthesis further includes a tubular knitted tubular graft circumferentially disposed and securably attached to the stent in the quiescent state. The graft has a single layer of yarns interlaced into stitches in a knit pattern capable of resilient longitudinal elongation and resilient radial contraction of the graft to the elongated state. The graft has from 400 to 1,000 stitches per square centimeter to provide compliancy in the quiescent state. The knit pattern is a warp knitted pattern of yarns forming a textile layer having an interior surface and an exterior surface, wherein interior yarns predominate the interior surface and form loops in the longitudinal direction of the prosthesis, and exterior yarns predominate the exterior surface and are diagonally shifted over two or more of the interior yarns in an alternating pattern along a width of the prosthesis before engaging an interior yarn.

In another aspect of the present invention, the prosthesis includes a longitudinally expandable stent and an expandable warp knitted graft having a single layer of yarns to define a single layered graft wall having a thickness from 0.3 to 0.4 millimeters. The yarns are interlaced into stitches in a knit pattern capable of resilient longitudinal elongation and resilient radial contraction of the graft to an elongated state. The graft has greater than 350 stitches per square centimeter to provide compliancy in its quiescent state. The knit pattern is a warp knitted pattern of yarns forming a textile layer having an interior surface and an exterior surface, wherein interior yarns predominate the interior surface and form loops in the longitudinal direction of said prosthesis, and exterior yarns predominate the exterior surface and are diagonally shifted over two or more of the interior yarns in an alternating pattern along a width of the prosthesis before engaging an interior yarn.

In still another aspect of the present invention, the prosthesis includes a longitudinally expandable stent and an expandable warp knitted graft having a single layer of yarns to define a single layered graft wall. The yarns are interlaced into stitches in a knit pattern capable of resilient longitudinal elongation and resilient radial contraction of the graft to an elongated state wherein the elongated length is from 50 to 200 percent by length greater than the quiescent length. The graft has greater than 350 stitches per square centimeter to provide compliancy in its quiescent state. The knit pattern is a warp knitted pattern of yarns forming a textile layer having an interior surface and an exterior surface, wherein interior yarns predominate the interior surface and form loops in the longitudinal direction of said prosthesis, and exterior yarns predominate the exterior surface and are diagonally shifted over two or more of the interior yarns in an alternating pattern along a width of the prosthesis before engaging an interior yarn.

In a further aspect of the present invention, the prosthesis includes a longitudinally expandable stent and an expandable warp knitted graft having a single layer of yarns to define a single layered graft wall. The yarns are interlaced into stitches in a knit pattern capable of resilient longitudinal elongation and resilient radial contraction of the graft to an elongated state. The graft has greater than 350 stitches per square centimeter to provide compliancy in its quiescent state. The knit pattern is a warp knitted pattern of yarns forming a textile layer having an interior surface and an exterior surface, wherein interior yarns predominate the interior surface and form loops in the longitudinal direction of said prosthesis, and exterior yarns predominate the exterior surface and are diagonally shifted over two or more of the interior yarns in an alternating pattern along a width of the prosthesis before engaging an interior yarn. The stent and the graft are resiliently deformable between the quiescent and the elongated states and the graft is capable of non-bulging contraction from the elongated state to the quiescent state to circumferentially abut the stent.

In other aspects of the present invention, a non-textile, desirably ePTFE, layer is provided with the endoprosthesis of the present invention. Furthermore, an implantable medical fabric is provided. The medical fabric is a knitted textile with a high degree of stretchability because of the warp knit pattern with at least a two needle underlap used to form the fabric. Moreover, a method for warp knitting a tubular graft with a warp knit pattern with at least a two needle underlap.

BRIEF DESCRIPTION OF THE DRAWINGS

FIG. 1 is a partial cut-away perspective view of an endoprosthesis of the present invention having a stent and a graft both capable of longitudinal expansion or contraction.

FIG. 2 is a cross-sectional view of the stent-graft of FIG. 1 taken along the 2—2 axis.

FIG. 3 depicts the stent-graft of FIG. 2 having a longitudinally expanded length.

DETAILED DESCRIPTION OF THE INVENTION

Figure 4:
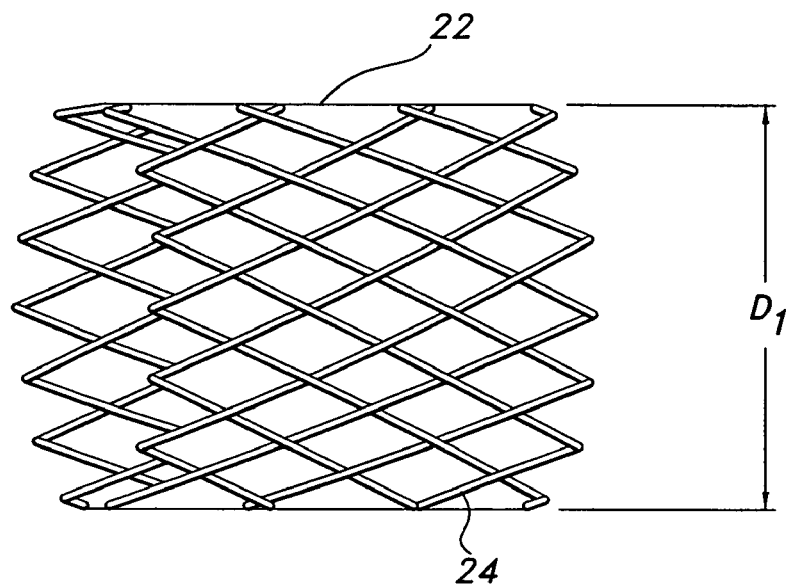
FIG. 4 depicts a wire stent in an expanded state according to the present invention.

The present invention addresses the problems associated with prior art stent-graph endoprosthesis. The stent-graft endoprosthesis of the present invention overcomes the disadvantages of presently available stent-grafts by providing an expandable graft that complements an expandable stent in both an expanded or contracted state and that further substantially inhibits dilation of the stent-graft after implantation into a bodily lumen. Furthermore, the graft of the present invention is knitted textile graft which provides a constraint against undesirable radial expansion while also providing greater longitudinal stretchability than previously knitted or woven textile grafts. Moreover, the knitted textile graft of the present invention has a porosity to permit the ingrowth of cells for the stabilization of implanted endoprosthesis while also being generally impermeable to inhibit substantial leakage of blood therethrough.

FIG. 1 is a depiction of stent-graft 10 of the present invention. Stent-graft 10 is shown as a generally tubular structure with open ends 16, 18 to permit the passage of a bodily fluid therethrough. Stent-graft 10 includes textile graft 12 and stent 14. Textile graft 12 extends circumferentially about stent 14. Textile graft 12 is securably attached to stent 14. The attachment of textile graft 12 to stent 14 may be accomplished by mechanically securing or bonding the textile graft 12 and the stent 14 to one and the other. Mechanical securement includes, but is not limited to, the use of sutures, anchoring barbs, textile cuffs and the like. Bonding includes, but is not limited to, chemical bonding, for instance adhesive bonding, thermal bonding and the like.

As depicted in FIG. 1, the textile graft 12 circumferentially extends about an outer stent surface 20. The present invention, however, is not so limited and other stent-graft configurations may suitably be used with the present invention. For instance, textile graft 12 may be circumferentially positioned along an inner surface of stent 14. Moreover, the longitudinal lengths of the stent 14 and the textile graft 12 are not limited to substantially similar lengths as depicted in FIG. 1. For instance, textile graft 12 may be shorter than stent 14 thereby leaving a portion of stent 14 without being covered by textile graft 12.

FIG. 2 dimensionally depicts the stent-graft 10 of the present invention after securement within a bodily lumen (not shown) and FIG. 3 dimensionally depicts the stent-graft 10' prior to securement thereat. To navigate the stent-graft within a bodily lumen the nominal diameter, $D_2$, of stent-graft 10' is smaller than the diameter, $D_1$, of stent-graft 10. Correspondingly, the length, $L_2$, of stent-graft 10' is larger than the length, $L_1$, of stent-graft 10. The textile graft 12 and the stent 14 both conform to these general dimensional depictions for the navigation and securement of stent-graft 10 within a bodily lumen. The textile graft 12 is elongated or stretched to accommodate the elongated stent-graft 10'. Correspondingly, textile graft 12 is in a substantially quiescent state to accommodate the stent-graft 10 of FIG. 2. Moreover, textile graft 12 is designed not to radially expand to a diameter substantially greater than the diameter D1 of stent-graft 10. Such a design substantially inhibits dilation of stent-graft 10.

Various stent types and stent constructions may be employed in the invention. Useful stents include, without limitation, self-expanding stents and balloon expandable stents. The stents may be capable of radially contracting or expanding, as well, and in this sense can be best described as radially or circumferentially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

The configuration of stent 14 may be of any suitable geometry. As shown in FIG. 4, wire stent 22 is a hollow tubular structure formed from wire strand 24 being arranged in what can be described as a "Z" or a "zig-zag" pattern. Wire strand 24 may be formed by, for example, braiding or spinning it over a mandrel. Alternatively, wire stent 24 may be formed from more than one wire strand.

Figure 5:
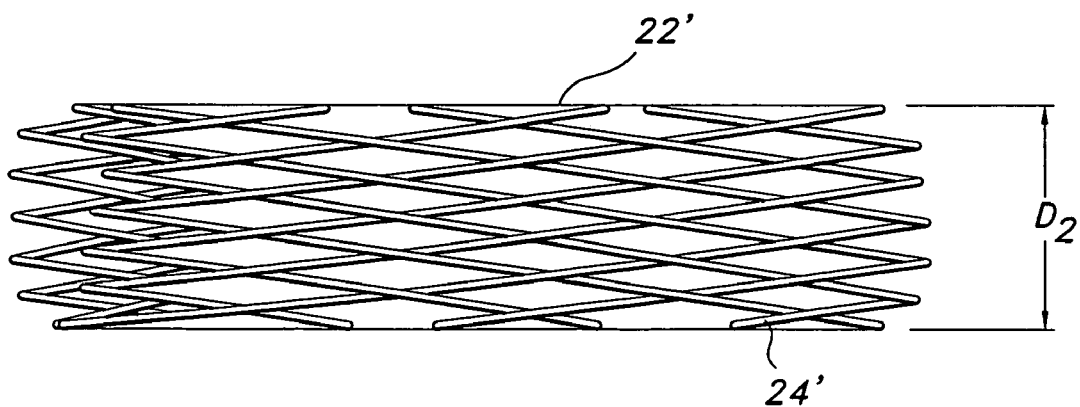
FIG. 5 depicts the wire stent of FIG. 5 in an unexpanded state.

Wire stent 22 is capable of being radially compressed and longitudinally extended, to yield wire stent 22', as depicted in FIG. 5, for implantation into a bodily lumen. The degree of elongation depends upon the structure and materials of the wire stent 22 and can be quite varied. For example, the length of wire stent 22' is from about 50% to about 200% of the length of wire stent 22. The diameter of wire stent 22' may also be up to several times smaller than the diameter of wire stent 22.

Figure 6:
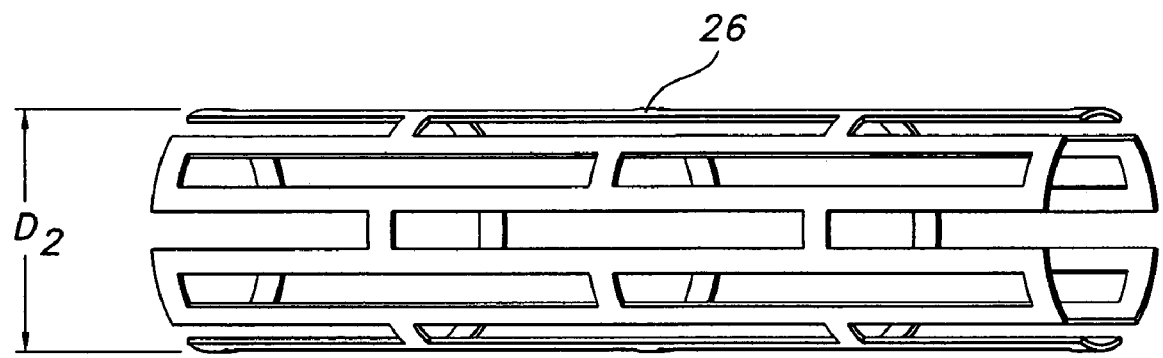
FIG. 6 depicts a slotted stent in a quiescent state according to the present invention.
Figure 7:
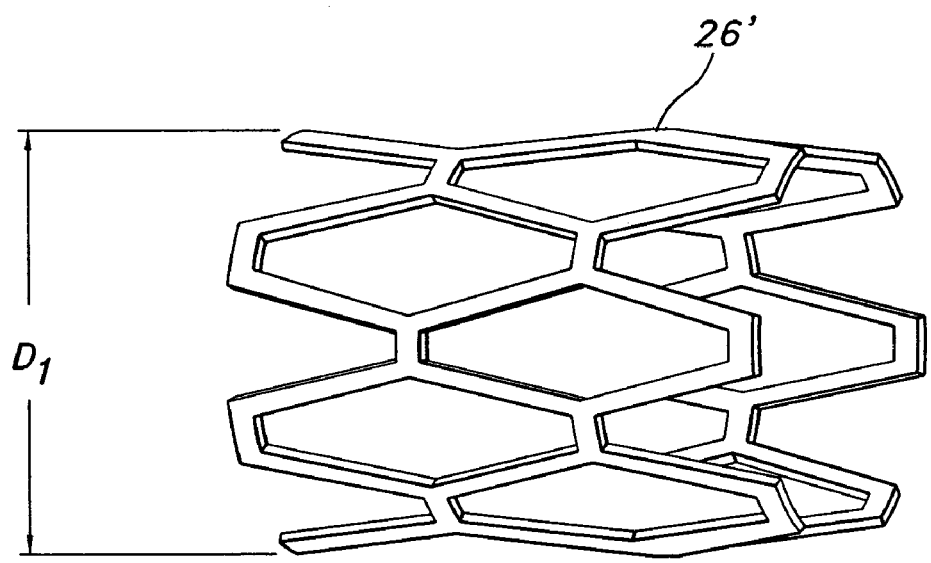
FIG. 7 depicts the slotted-stent of FIG. 6 in an expanded state.

In another aspect of the present invention, a slotted stent 26 is also useful as part of the stent-graft 10. As depicted in FIG. 6, slotted stent 26 is suitably configured for implantation into a bodily lumen (not shown). Upon locating the slotted stent 26 at the desired bodily site, slotted stent 26 is radially expanded and longitudinally contracted for securement at the desired site. The expanded slotted stent 26' is depicted in FIG. 7. Slotted stent 26' is from about 50% to about 200% greater in radial dimension as compared to slotted stent 26.

Figure 8:
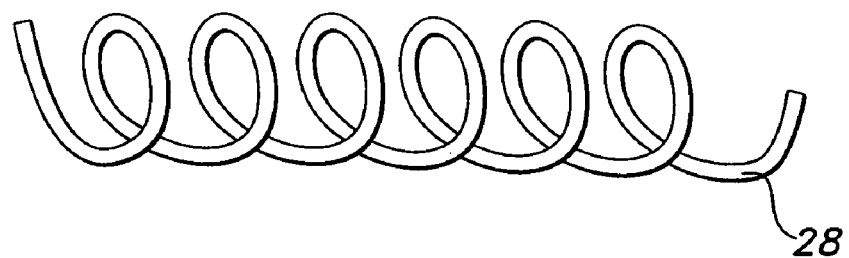
FIG. 8 is a perspective view of a helical coil formed of a single wound wire.
Figure 9:
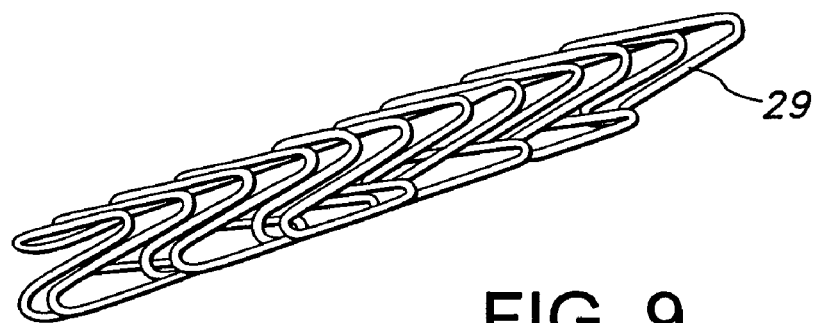
FIG. 9 is a perspective view of a stent having an elongate pre-helically coiled configuration.
Figure 10:
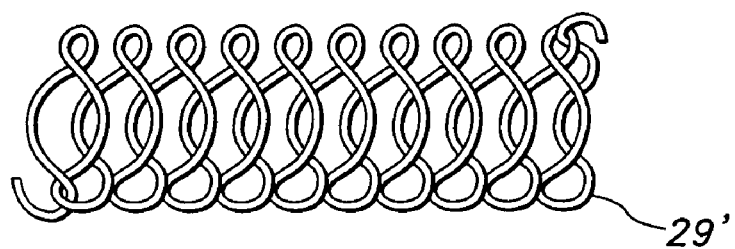
FIG. 10 is a perspective view of the stent of FIG. 9 in a radially expanded state.

Other useful stents capable of radial expansion are depicted in FIGS. 8, 9 and 10. As depicted in FIG. 8, stent 28 is a helical coil which is capable of achieving a radially expanded state (not shown). Stent 29, as depicted in FIG. 9, has an elongate pre-helically coiled configuration as shown by the waves of non-overlapping undulating windings. Stent 29 is capable of being radially expanded to expanded stent 29' as depicted in FIG. 10. These helically coiled or pre-helically stents are also useful with the practice of the present invention.

The textile graft 12 is a knitted textile graft. Knitting involves the interlooping or stitching of yarn into vertical columns (wales) and horizontal rows (courses) of loops to form the knitted fabric structure. Warp knitting is particularly useful with the textile graft 12 of the present invention. In warp knitting, the loops are formed along the textile length, i.e., in the wale or warp direction of the textile. For a tubular textile, such as textile graft 12, stitches in the axial or longitudinal direction of the tubular textile are called wales and stitches in the axial or circumferential direction of the tubular textile are called courses.

Conventional knitted tubular grafts often had to reduce the number of wales per inch to reduce the tendency of a graft to dilate. A low number of wales per inch, however, often reduces compliance of the graft where the graft may not be fluid-tight, i.e., prevent flow of blood therethrough, without other sealing mechanisms. Conventional grafts also used inelastic or a combination of inelastic and elastic yarns to limit radial expansion of a knitted textile graft. The textile graft 12 of the present invention is not so limited. The textile graft 12 uses a novel knit pattern which by itself substantially inhibits undesirable radial expansion. Moreover, the knit pattern of the present invention allows for radial contraction and longitudinal elongation of the textile graft 12 while still providing a constraint to limit radial expansion.

Moreover, conventional knitted tubular grafts often had to reduce or limit the number of courses per inch to obtain a flexible tubular structure, i.e., a structure with longitudinal stretchability. Reducing the number of courses per inch, however, opens the macroporous structure of the textile. A macroporous textile structure is not desirable as a graft because such a structure is not a fluid tight structure, i.e., blood will flow through the graft. Similarly, if the number of wales per inch was too low, the graft would not seal blood flow. If the number of wales per inch was too high, the graft could dilate with time. Thus, conventional grafts were limited by the total number of courses and wales per inch, which is referred to as the number of picks per square inch or the pick size.

For example, U.S. Pat. No. 5,732,572 to Litton describes a textile tubular prosthesis in a warp-knit having a underlap of greater than two needle spaces to limit dilation. The prosthesis, however, is limited to a pick size of 80 to 350 stitches per square centimeter (6,400 to 2,260 stitches per square inch) to provide a longitudinally stretchable tubular structure. Such a pick size represents about 9 to 19 courses or wales per centimeter (23 to 48 courses or wales per inch). With such a low pick size the prosthesis of this patent is knitted in multiple layers to provide a fluid tight structure while maintaining some degree of stretchability and resistance to dilation. The textile graft 12 of the present invention is not so limited because of the novel knit pattern used to form the graft as compared to more conventional knit patterns, such as tricot, locknit and the like, or even other stretchable knit patterns interlaced with these patterns.

Moreover, grafts are sometimes crimped with creases or folds which tend to reduce kinking when the graft is bent. The kinking also allows for some elongation of the graft, but such a crimped graft would not be generally useful as a stent-graft because of the gaps that would result between the stent and the crimped graft.

The textile graft 12 is configured to have a high degree of stretchability. As used herein, the term stretchability and its variants refers to a textile capable of substantially reversible elongation between a quiescent state and a stretched state. Desirably, the stretchability of the textile graft 12 is substantially compatible with the dimensional changes associated with an expandable stent having both a expanded and an unexpanded or a contracted state as discussed above. Moreover, textile graft 12 is not a crimped graft and does non-bulgingly contract from the elongated state to the quiescent state. The textile graft 12 substantially abuts the stent along both circumferential and longitudinal portions of the stent without separating or bulging from the stent.

Knitting patterns useful in providing desirable limits to radial expansion while maintaining the desired longitudinal stretchability include those knitting patterns that are not highly interlaced, such as patterns that interlace each adjacent back and front yarn. An example of a highly interlaced and commonly known knitted pattern is a Tricot or Jersey pattern. In contrast the knitting pattern of the present invention is not highly interlaced to provide, among other things, the stretchability of the textile graft for use with an expandable stent.

Figure 11:
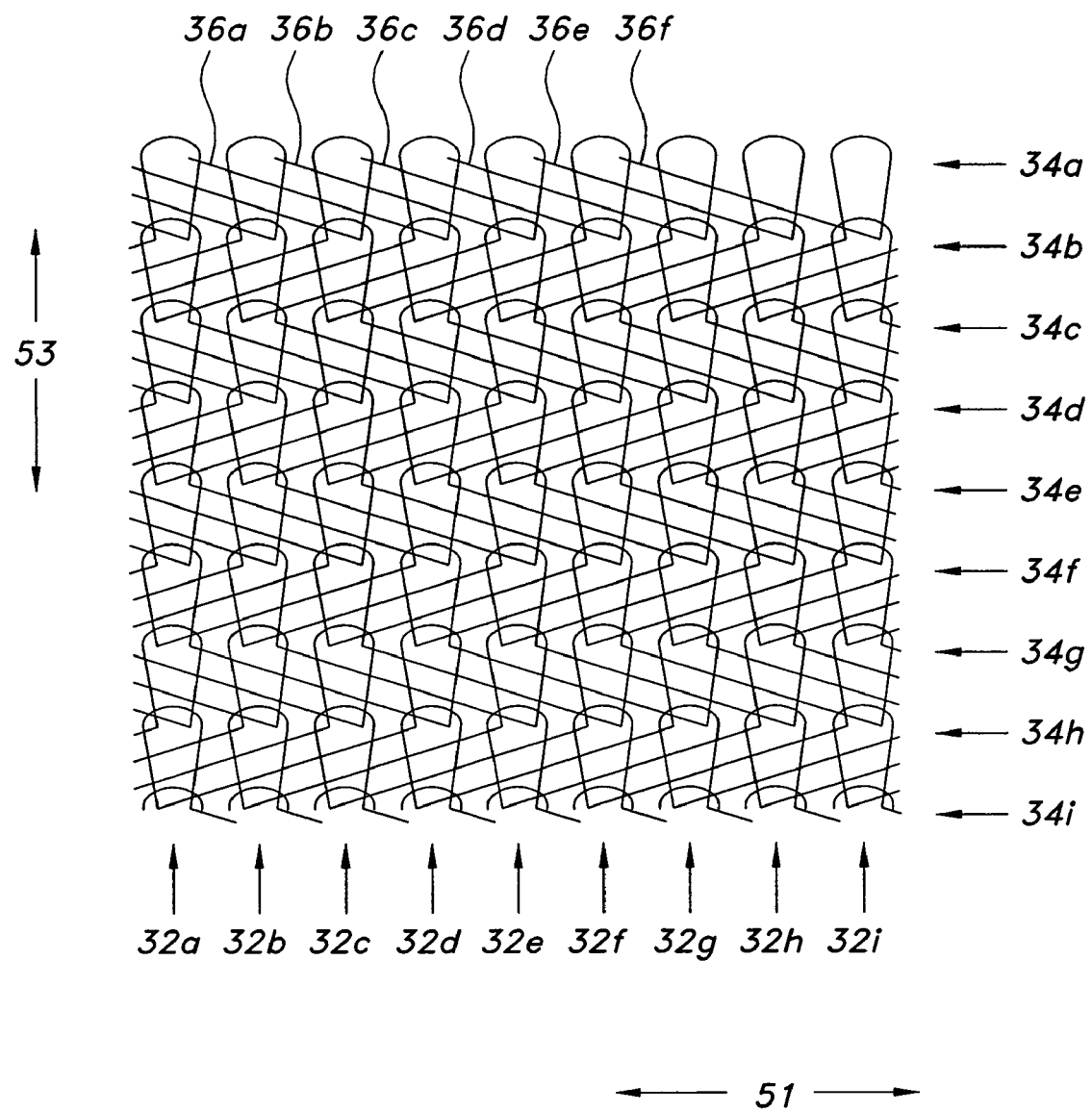
FIG. 11 is an illustration of a textile portion of the graft of FIG. 1 taken along the 11—11 axis.

FIG. 11 is an illustration of portion 30 of textile graft 12 taken along the 11—11 axis. The knitted portion 30 is characterized as a three needle underlap. In FIG. 11, needle positions in the course direction, i.e., vector 51, are noted by element numbers 32a through 32i and needle positions in the wale direction, i.e., vector 53, are noted by element numbers 34a through 34i. Yarn 36a travels in the course direction from needle position 32a to needle position 32d, or three needle positions, before interlooping with yarn 36d. Yarn 36a then travels three needle positions in the opposite course direction to interloop with a yarn. This alternating three needle position movement is repeated with different yarns to form a knitted pattern with a three needle underlap.

The knitted portion 30 is depicted as a single knitted layer in FIG. 11, however, the textile graft 12 of the present invention is not so limited. For instance, the knitted portion 30 may include more than one layer of interconnected yarns. In such a multi-layered knitted textile, yarns from one layer are often interlooped with yarns in another layer to form the multi-layered knitted textile.

Textile graft 12 is a flat-knitted tubular structure. To form such a flat-knitted tubular structure, two portions 30 are co-knitted and connected to one and the other joined together by border yarns.

Figure 12:
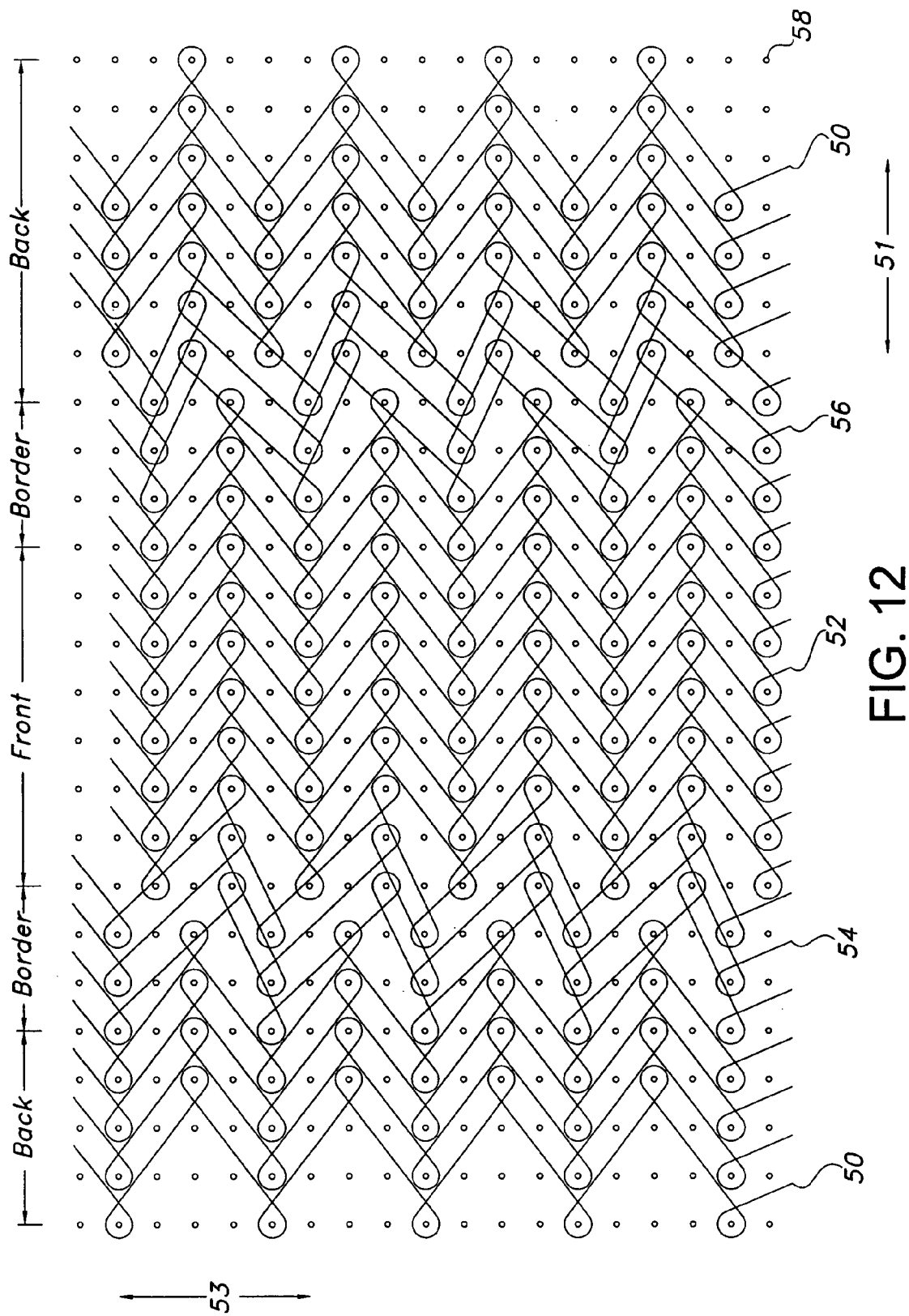
FIGS. 12 and 13 depict yarn patterns for the textile portion of FIG. 8.

FIG. 12 depicts the yarn patterns of FIG. 11 by separating the front, back and border yarns from one and the other to more clearly illustrate the individual yarn knit pattern and the repeating nature, if any, of these individual yarn knit patterns. As depicted in FIG. 12, front yarn 52 and back yarn 50 are repeated about 8 times. Border yarns 54 and 56 alternately repeat about three between the repeating front and back yarn patterns. The front yarn pattern is repeated to yield the technical front or the exterior surface of the textile graft 10 of the present invention. The back yarn pattern is repeated to yield the technical back or the interior surface of the textile graft 10 of the present invention.

Figure 13:
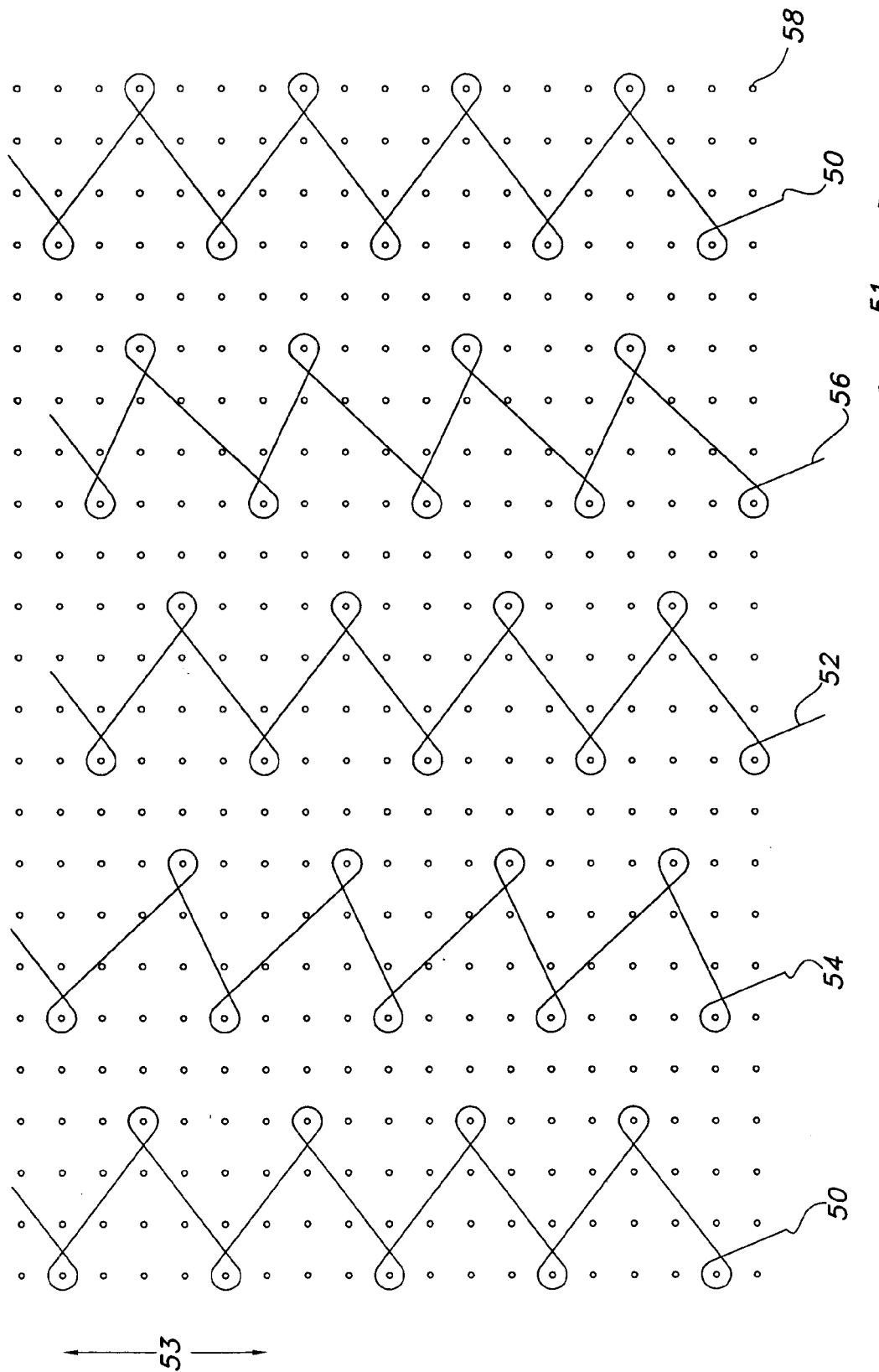

The knitting patterns for the front and back yarns are further illustrated in FIG. 13. The front, back and border yarns are interlaced in a relatively loose pattern having an underlap of at least three needle positions, which are depicted as dots 58. As used herein the term underlap and its variants refer to a yarn that traverses one or more yarns before forming an interlacing loop with a yarn. Such a pattern not only provides stretchability to the textile graft 12 but also provides resistance against dilation. Not wishing to be bound by any particular theory, it is believed that the long underlap in the course direction, which is indicated as vector 51, reduces the potential for expansion in the wale direction, which is indicated by vector 53, because the underlap in the course direction inhibits undesirable radial expansion.

As shown in FIG. 13, back yarns 50 and front yarns 52 shift diagonally by at least three needle positions in alternating closed-loop interlacing structures. As used herein, closed-loops refer to interlacing yarns where a front or a back yarn crosses over itself in forming the loop. Other patterns useful with the practice of the present invention, such as border patterns, are illustrated in FIG. 13.

To knit textile patterns useful with the present invention, double needle bar warp-knitting machine with multiple beams or guide bars is used to form a flat-knitted seamless tubular structure. The threading pattern for each guide bar is shown below in Table 1, and the arrangement of each needle for the guide bar is shown below in Table 2.

TABLE 1

Guide Bar Threading Details

| Guide Bar | y - Threaded/n - Not Threaded Settings | | | | | | | | | | |
|---|---|---|---|---|---|---|---|---|---|---|---|
| 8 | y | y | y | y | y | y | y | y | n | n | n |
| 7 | y | n | n | n | n | n | n | n | n | n | n |
| 6 | n | n | n | n | n | n | n | n | n | n | y |
| 5 | y | n | n | n | n | n | n | n | n | n | n |
| 4 | n | n | n | n | n | n | n | n | n | y | n |
| 3 | y | n | n | n | n | n | n | n | n | n | n |
| 2 | y | n | n | n | n | n | n | n | n | n | n |
| 1 | y | y | y | y | y | y | y | y | n | n | n |

TABLE 2

Guide Bar Positions

| Guide Bar | Positions | |
|---|---|---|
| 1 | 6-8-4-4/2-0-4-4/(repeat) | Front Full Thread |
| 8 | 4-4-2-0/4-4-6-8/(repeat) | Back Full Thread |
| 2 | 4-6-2-2/0-0-0-2/(repeat) | Right Connect |
| 4 | 2-4-0-0/2-2-2-4/(repeat) | Right Connect |
| 6 | 0-2-2-2/4-4-4-6/(repeat) | Right Connect |
| 3 | 2-2-2-0/6-4-4-4/(repeat) | Left Connect |
| 5 | 4-4-4-2/4-2-6-6/(repeat) | Left Connect |
| 7 | 6-6-6-4/2-0-4-4/(repeat) | Left Connect |

The knitted textile graft of the present invention is desirably made on a warp-knitting machine (not shown) using a double needle bar. A useful number of needles per inch for warp knitting is from about 18 to about 36. About 28 needles per inch are particularly suitable. The trellis of the graft is usually made from a yarn having count from 30 to 300 denier. Desirably, the range of yarn counts for the trellis is from about 30 to about 80. A particularly suitable yarn count is about 40 denier. Moreover, the trellis yarn may be a single ply, a double ply or a multi-ply. The term "multi-ply" is used herein to indicate more than two-ply.

Furthermore, the knitted textile graft of the present invention has greater than 350 stitches per square centimeter, for instance from about 400 to about 1,000 stitches per square centimeter (about 2,600 to about 6,500 stitches per square inch), to provide compliancy of the graft. Desirably, the present invention has from about 650 to about 800 stitches per square centimeter (about 4,200 to about 5,200 stitches per square inch). Moreover, the knitted textile graft of the invention has from about 15 to about 50 courses or wales per centimeter (about 40 to about 130 courses or wales per inch) to provide compliancy of the graft. The number of courses and wales per unit length may be the same or different. Desirably, the present invention has from about 20 to about 50 wales per centimeter (about 50 to about 130 wales per present invention has from about 15 to about 32 courses per centimeter (about 40 to about 80 courses per inch).

In one aspect of the present invention, the knitted textile graft is a knit structure of a single layer with at least a two-needle underlap. Because of the single layer construction the textile wall thickness is minimized to yield a low profile knitted textile graft. The textile wall thickness is from about 0.3 to about 0.4 millimeters. Desirably, the textile wall thickness is from about 0.33 to about 0.36 millimeters. Furthermore, the knitted textile graft of the present invention has a burst strength from about 12 kg/cm$^2$ to about 16 kg/cm$^2$ (about 160 psi to about 220 psi). Desirably, the knitted textile graft of the present invention has a burst strength from about 13 kg/cm$^2$ to about 14 kg/cm$^2$ (about 180 psi to about 200 psi). The stretchability of the knitted textile graft is 50 to 200 percent at a one-kilogram of load. Knitted textile grafts with a stretchability of about 80 to 200 percent at one-kilogram load are also useful. Furthermore, knitted textile grafts with a stretchability of about 120 to 160 percent at one-kilogram load are also useful.

In a typical method of warp knitting the back yarn is fed from two inside beams, each beam being a spool holding a plurality of ends. Outside beams may be used in conjunction with the inside beams; the outside beams being used for feeding the front yarns. Each outside beam also has a plurality of ends. It should be noted, however, that the inside beams may be used for feeding the front yarn and the outside beams used for feeding the back yarn. Regardless of which beams are used, texturized flat yarn is generally used for both the front and back yarns. The minimum number of beams used in making the textile graft of the present invention is 2. A greater number of beams, however, may be found useful for specific applications. Eight guide beams or guide bars have been found to be particularly useful with the practice of the present invention.

Any type of textile product can be used as yarns for the knitted textile graft of the present invention. Of particular usefulness in forming the knitted fabric prosthesis of the present invention are synthetic materials such as synthetic polymers. Synthetic yarns suitable for use in the present invention include, but are not limited to, polyesters, including PET polyesters, polypropylenes, polyethylenes, polyurethanes and polytetrafluoroethylenes. The yarns may be of the monofilament, multifilament, spun type or combinations thereof. The yarns may also be flat, twisted or textured, and may have high, low or moderate shrinkage properties or combinations thereof.

The yarns used in forming the textile grafts of the present invention may be flat, twisted, textured or combinations thereof. Furthermore, the yarns may have high, low or moderate shrinkage properties or combination of different shrinkage properties. Additionally, the yarn type and yarn denier can be selected to meet specific properties desired for the prosthesis, such as porosity and flexibility. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 200, preferably from about 30 to about 100. Preferably, the yarns are polyester, such as polyethylene terephthalate (PET), and more preferably the yarns are one ply, 40 denier, 27 filament flat and texturized polyester.

After knitting the textile graft of the present invention is optionally cleaned or scoured in a basic solution of warm water, e.g., about 50° C. to about 65° C. (about 120° F. to about 150° F.), and detergent. The textile is then rinsed to remove any remaining detergent.

After the textile graft is optionally scoured, the graft is compacted or shrunk to reduce and control, in part, the porosity of the graft. Porosity of a knitted material is measured on the Wesolowski scale and by the procedure of Wesolowski. In the Wesolowski test, a fabric test piece is clamped flatwise and subjected to a pressure head of about 120 mm. of mercury. Readings are obtained which express the number of millimeters of water permeating per minute through each square centimeter of fabric. A zero reading represents absolute water impermeability and a value of about 20,000 represent approximate free flow of fluid.

The porosity of the textile graft 12 is often from about 7,000 to about 15,000 on the Wesolowski scale after being knitted on the double needle bar Raschel knitting machine. A more desirable porosity is from about 30 to about 5,000 on the Wesolowski scale and textile graft is compacted or shrunk in the wale direction to obtain the desired porosity. A solution of an organic component, such as hexafluoroisopropanol or trichloroacetic acid, and a halogenated aliphatic hydrocarbon, such as methylene chloride, is used to compact the textile graft by immersing it into the solution for up to 30 minutes at temperatures from about 15° C. to about 160° C. Other compacting solutions may suitably be used, such as those disclosed in U.S. Pat. Nos. 3,853,462 and 3,986,828, whose contents are incorporated by reference herein.

As noted above, preferably the tubular-knitted graft of the present invention is constructed of polyester which is capable of shrinking during a heat-set process. For instance, such grafts are typically flat-knitted in a tubular form. Due to the nature of the flat-knitting process, the tubular graft is generally flat in shape after knitting. Such grafts, however, when constructed of shrinkable polyester yarn, can be heat set on a mandrel to form a generally circular shape.

Such a heat-setting process is accomplished by first knitting the graft in a seamless tubular form out of a material capable of shrinking during a heat-setting or similar process. The graft may be preshrunk before it is placed on a mandrel. Preshrinking may be achieved by submitting the woven graft to moderate temperatures, such as from about 90° C. to about 205° C. (about 190° F. to about 400° F.). Usually the graft is placed in a medium for the preshrinking. Such a medium can include without limitation hot water, a chemical fluid, such as methylene chloride, or a gas, such as air or carbon dioxide. The graft of the present invention, however, may suitably be made without such a preshrinking of the yarns.

After the graft is knitted or alternatively knitted and preshrunk, the graft is placed on a mandrel, and heated in an oven at a temperature and time capable of causing the yarns of the graft to heat set to the shape and diameter of the mandrel. Preferably polyester yarns are used, and the heat setting is accomplished at time and temperatures appropriate for the material. For example, heat setting can be accomplished at about 90° C. to about 225° C. (about 190° F. to about 437° F.) for a period of about less than an hour. Temperatures in the range of about 130° C. to about 220° C. (about 260° F. to about 428° F.) are also useful. Desirably, temperatures from about 150° C. to about 215° C. (about 300° F. to about 419° F.) are also useful. Desirably, time periods from about 5 to about 30 minutes are useful. More desirably, with time periods from about 10 to about 20 minutes are useful. Other methods of heat setting known in the art may be employed. After such a heat setting process, the graft can be formed into a shape desired for implantation, having a generally circular inner lumen.

Figure 14:
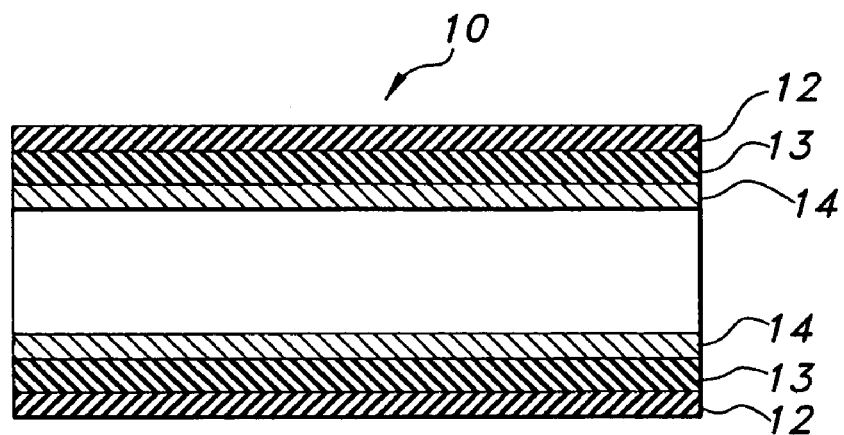
FIG. 14 is a cross-sectional of the present invention which further includes a layer of e-PTFE.

In another aspect of the present invention stent-graft 10 further includes a non-textile layer 13, as depicted in FIG. 14. The non-textile layer is circumferentially disposed between textile graft 12 and stent 14 and securably attached therebetween. One type of non-textile material particularly useful is polytetrafluoroethylene (PTFE). PTFE exhibits superior biocompatibility and low thrombogenicity, which makes it particularly useful as vascular graft material in the repair or replacement of blood vessels. Desirably the non-textile layer is a tubular structure manufactured from expanded polytetrafluoroethylene (ePTFE). The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to 600 percent by linear dimension. The physically modified ePTFE tubular structure is able to be elongated or expanded and then returned to its original state without an elastic force existing therewithin. Such a physically modified ePTFE tubular structure is advantageously used in conjunction with wire-stent 22 of stent-graft 10.

Figure 16:
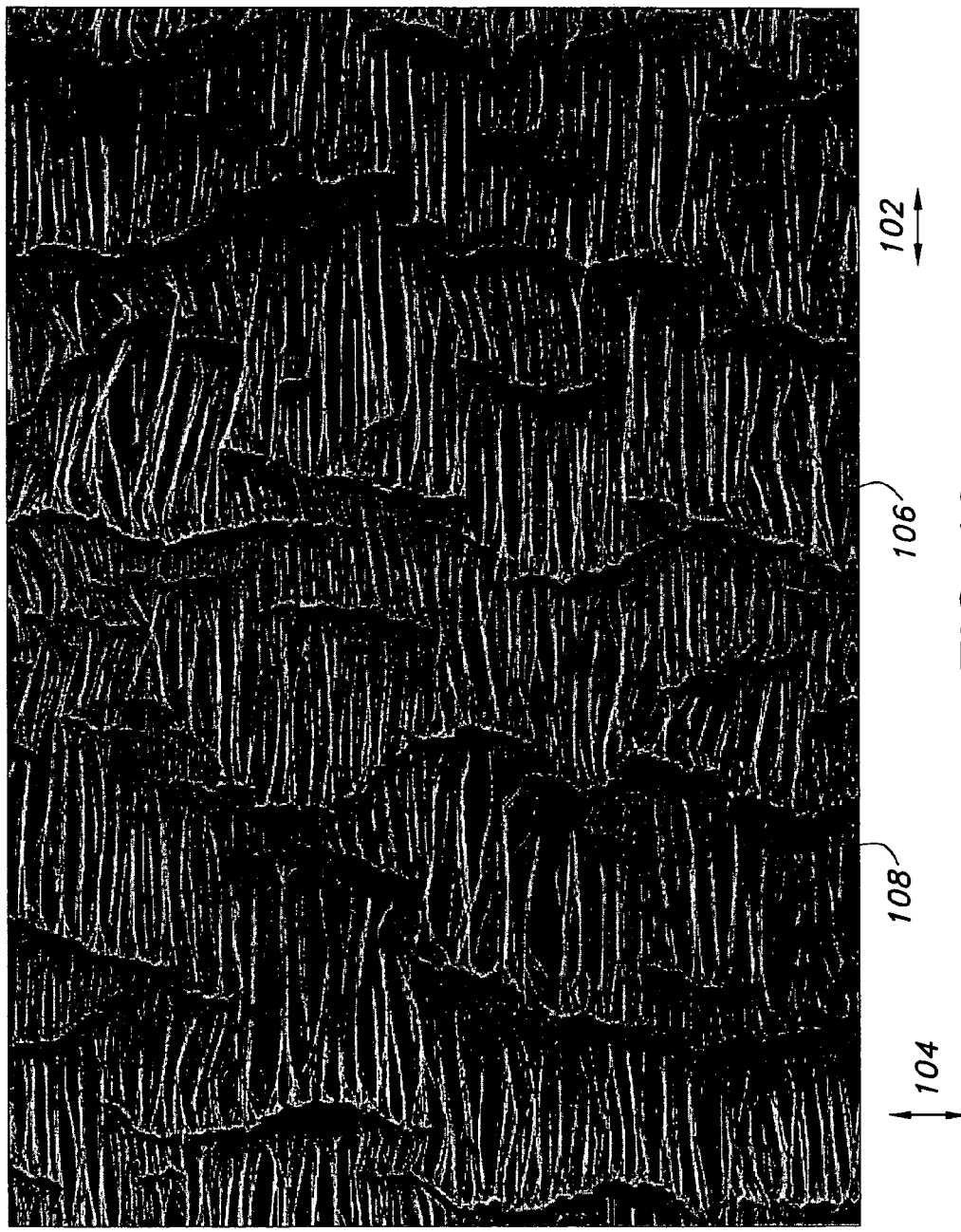
FIG. 16 is a photomicrograph showing a longitudinally expanded ePTFE structure.

FIG. 16 is a photomicrograph of a traditionally longitudinally expanded ePTFE tubular structure. The tube has been stretched in the longitudinal direction shown by directional arrow 102, leaving the nodes circumferentially oriented in circumferential direction shown by the directional arrow 104. The fibrils 106 are shown as being uniformly oriented in the longitudinal direction shown by directional arrow 102. Nodes 108 are shown and are uniformly oriented in circumferential direction 104.

Figure 17:
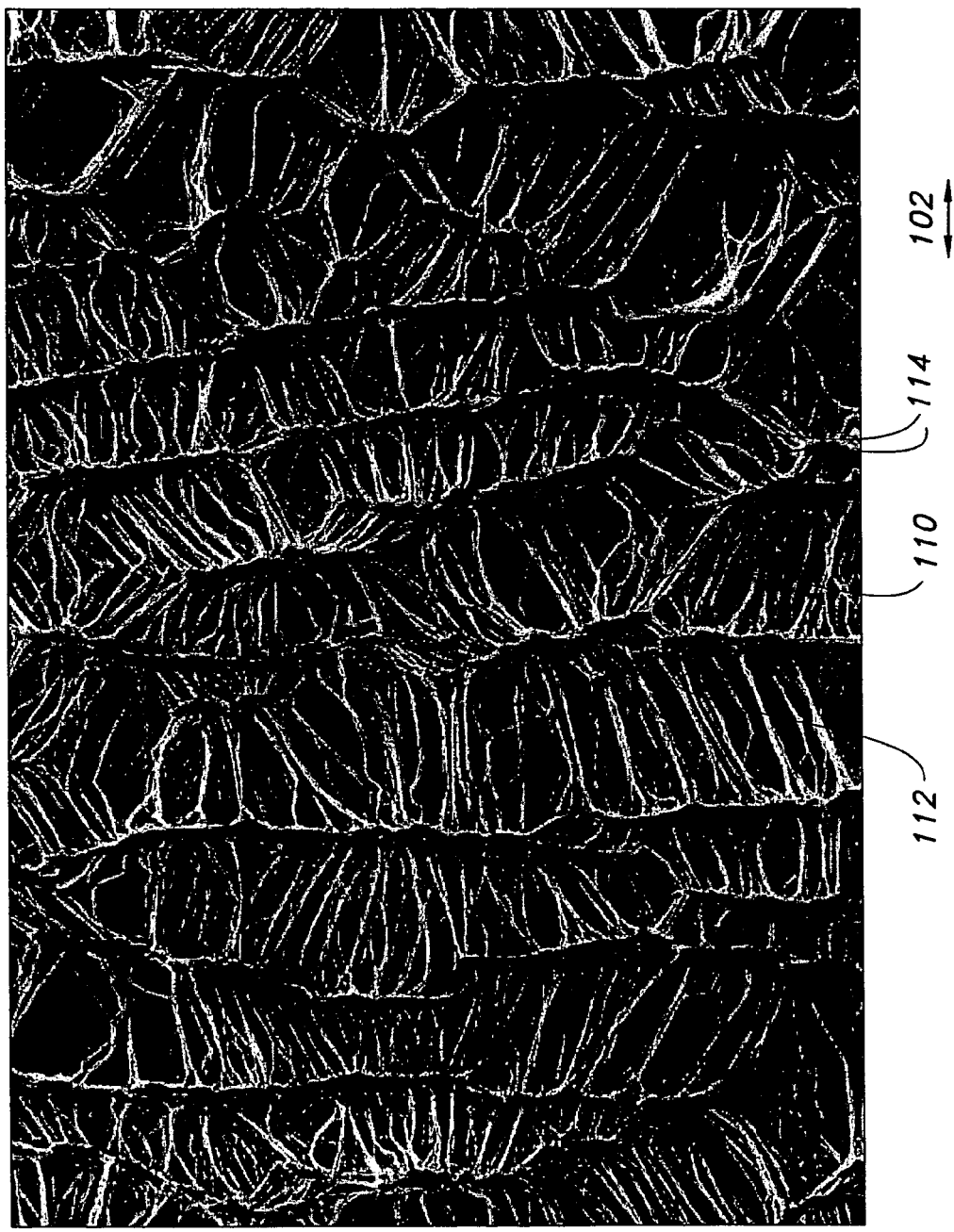
FIG. 17 is a photomicrograph of physically modified ePTFE structure having enhanced elongation properties as compared to the ePTFE structure of FIG. 16.

FIG. 17 is a photomicrograph of the physically modified ePTFE tubular structure having circumferentially oriented nodes and longitudinally traversing fibrils. Nodes 110 are shown in the photomicrograph with a set of fibrils with first ends 112 and second ends 114 attached thereto. The fibrils with first ends 112 and second ends 114 are shown in a hingeably rotated position so that they are not substantially longitudinally oriented in the direction shown by directional arrow 102 as compared to the substantially longitudinally oriented parallel fibril structures 106 of FIG. 13. The term "hingeably rotated" and variants thereof refer to reorientation of previously uniformly oriented line segments by a change in position of one end of each line segment in relation to the other end of each segment, which remains fixed; i.e., the "hinge" about which the other end rotates. The reorientation takes place without a substantial change in dimension of the line segment. Additional details of the physically-modified ePTFE and methods for making the same can be found in commonly assigned application titled, "ePTFE Graft With Axial Elongation Properties", filed on date herewith, application Ser. No. 09/898,415, the contents of which are incorporated by reference herein.

Figure 15:
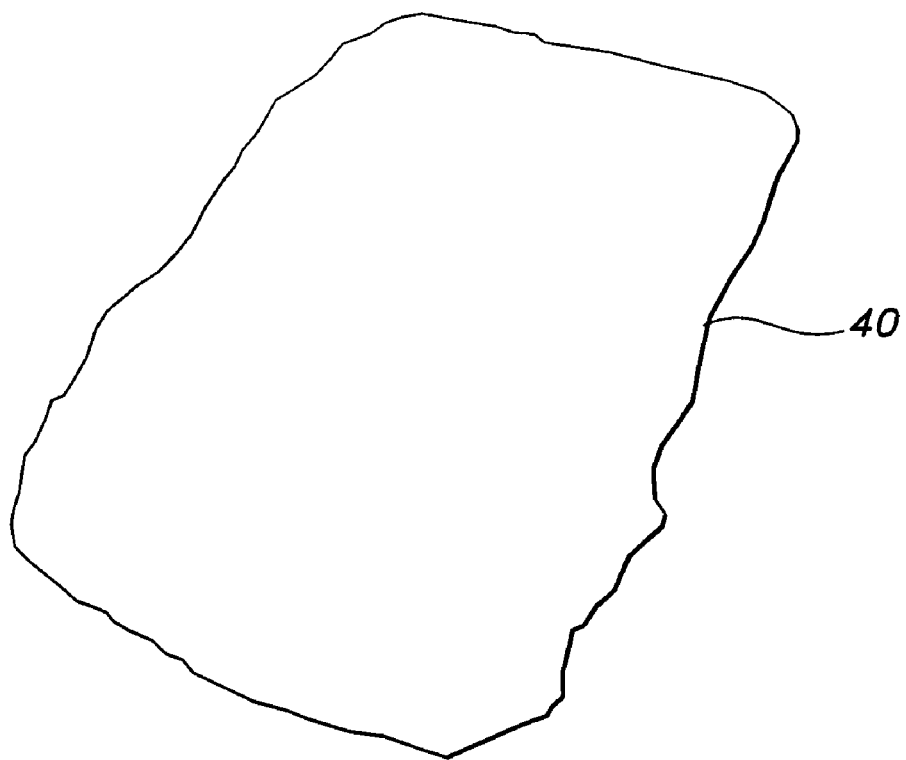
FIG. 15 is a partial perspective view of a knitted medical fabric of the present invention.

FIG. 15 is a partial perspective view of an implantable medical fabric 40, another aspect of the present invention. The medical fabric 40 is a warp-knitted textile fabric having at least a two needle underlap as described above. The medical fabric 40 has the features of the above-described textile graft 12, for instance, a high degree of stretchability. The medical fabric 40 of the present invention is useful in intraluminal applications, such as hernia repair.

The invention may be further understood with reference to the following non-limiting examples.

EXAMPLES

Example 1

Single Layer Knit Tubular Graft with a Three Needle Underlap

The following specifications are used to fabricate a solid knitted prosthesis of the present invention.

Yarn Type: Texturized polyethylene terephthalate (PET), 40 denier, 27 filaments.

Machine Type: 56 Guage Kidde machine.

Number of Guide Bars: Eight

Guide Bar Threading Details: (y-Threaded/n-Not Threaded)

Guide Bar No. 8: y/y/y/y/y/y/y/y/n/n/n
Guide Bar No. 7: y/n/n/n/n/n/n/n/n/n
Guide Bar No. 6: n/n/n/n/n/n/n/n/n/y
Guide Bar No. 5: y/n/n/n/n/n/n/n/n/n
Guide Bar No. 4: n/n/n/n/n/n/n/n/y/n
Guide Bar No. 3: y/n/n/n/n/n/n/n/n/n
Guide Bar No. 2: y/n/n/n/n/n/n/n/n/n
Guide Bar No. 1: y/y/y/y/y/y/y/y/n/n Guide Bar Position Details:

Guide Bar No. 1: 6-8-4-4/2-0-4-4/(repeat) Front Full Thread
Guide Bar No. 8: 4-4-2-0/4-4-6-8/(repeat) Back Full Thread
Guide Bar No. 2: 4-6-2-2/0-0-0-2/(repeat) Right Connect
Guide Bar No. 4: 2-4-0-0/2-2-2-4/(repeat) Right Connect
Guide Bar No. 6: 0-2-2-2/4-4-4-6/(repeat) Right Connect
Guide Bar No. 3: 2-2-2-0/6-4-4-4/(repeat) Left Connect
Guide Bar No. 5: 4-4-4-2/4-2-6-6/(repeat) Left Connect
Guide Bar No. 7: 6-6-6-4/2-0-4-4/(repeat) Left Connect Graft Processing:

Subsequent to knitting the textile graft, the material is scoured in a basic solution of warm water (e.g., about 65° C. or about 150° F.) and cleaning detergent. It is then rinsed to remove the cleaning agents. The graft is then compacted with methylene chloride at elevated temperatures, for instance about 107° C. or about 224° F. for a short period of time, for instance, three minutes.

Next, the prosthesis is heat-set on stainless steel mandrels to achieve the final desired inside diameter. Typically, the outside diameter of the mandrel is typically twenty to forty percent oversized to impart, in part, high stretch and low dilation characteristics to the textile graft. Heat setting can take place in a convection oven at about 212° C. (about 414° F.) for about 10 minutes.

As a result of the heat setting, the warp yarns are locked in the knitted geometry with a three-needle underlap to build in "spring like" properties that capable of longitudinal expansion. The heat set graft is capable of about 50 to 200 percent longitudinal expansion.

Example 2

Single Layer Stretch Knit Straight Tubular Graft with a Two-needle Underlap

The following specifications were used to fabricate a super stretch knitted prosthesis of the present invention.

Yarn Type Used: Texturized polyethylene terephthalate (PET), 40 denier, 27 filaments.

Machine Used: 56 gauge Kiddie machine

Guide Bars Used: 6

| Guide Bar Threading Details: (y - threaded, n - not threaded): | | | | | | | | | | | |
|---|---|---|---|---|---|---|---|---|---|---|---|
| Guide Bar No. 6 | n | n | y | y | y | y | y | y | y | y | n |
| Guide Bar No. 5 | n | y | n | n | n | n | n | n | n | n | n |
| Guide Bar No. 4 | n | n | n | n | n | n | n | n | n | n | y |
| Guide Bar No. 3 | n | n | n | n | n | n | n | n | n | y | n |
| Guide Bar No. 2 | y | n | n | n | n | n | n | n | n | n | n |
| Guide Bar No. 1 | n | n | y | y | y | y | y | y | y | y | n |

| Guide Bar Chain Notation Details: | | |
|---|---|---|
| Guide Bar No. 1: | 2-0/4-4/4-6/2-2//repeat | Front full thread |
| Guide Bar No. 2: | 4-2/4-4/2-2/2-0//repeat | Left connector |
| Guide Bar No. 3: | 2-2/2-4/0-2/0-0//repeat | Right connector |
| Guide Bar No. 4: | 0-0/0-2/2-4/2-2//repeat | Right connector |
| Guide Bar No. 5: | 2-0/2-2/4-4/4-2//repeat | Left connector |
| Guide Bar No. 6: | 2-2/4-6/2-2/2-0//repeat | Back full thread |

Graft Processing:

Subsequent to knitting the textile graft, the material was scoured in a basic solution of warm water (e.g., about 65° C. or about 150° F.) and cleaning detergent. It was then rinsed to remove the cleaning agents. The graft was then compacted with methylene chloride at elevated temperatures, for instance about 107° C. or about 224° F., for a short period of time, for instance, three minutes.

Next, the prosthesis was heat-set on stainless steel mandrels to achieve the final desired inside diameter. Typically, the outside diameter of the mandrel was twenty to forty percent oversized to impart, in part, high stretch and low dilation characteristics to the textile graft. Heat setting was accomplished in a convection oven at about 212° C. (about 414° F.) for about 10 minutes.

As a result of the heat setting, the warp yarns were locked in the knitted geometry with a two-needle underlap to build in "spring like" properties that are capable of longitudinal expansion. The heat set graft was capable of about 50 to 200 percent longitudinal expansion.

Example 3

Single Layer Stretch Knit Bifurcated Tubular Graft with a Two-Needle Underlap

Figure 18:
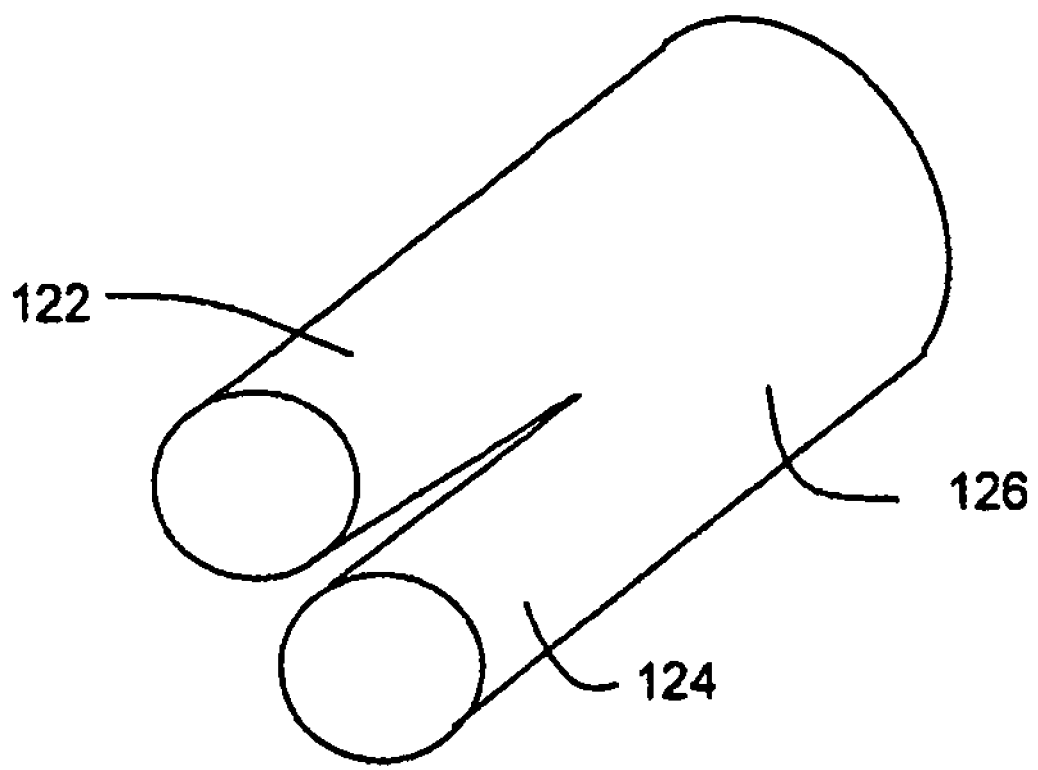
FIG. 18 is a perspective view of a bifurcated graft.

The following specifications were used to fabricate a bifurcated super stretch knitted prosthesis 120 of the present invention, which is depicted in FIG. 18 as having legs 122, 124 and a body 126.

Yarn Type Used: Texturized polyethylene terephthalate (PET), 40 denier, 27 filaments.
Machine Used: 56 gauge Kiddie machine
Guide Bars Used: 10

| Guide Bar Threading Details: (y - threaded, n - not threaded): | | | | | | | | | | | | |
|---|---|---|---|---|---|---|---|---|---|---|---|---|
| Guide Bar No. 10 | n | n | y | y | y | y | n | n | y | y | y | n |
| Guide Bar No. 9 | n | y | n | n | n | n | n | n | n | n | n | n |
| Guide Bar No. 8 | n | n | n | n | n | n | n | n | n | n | n | y |
| Guide Bar No. 7 | n | n | n | n | n | y | n | n | n | n | n | n |
| Guide Bar No. 6 | n | n | n | n | n | n | n | y | n | n | n | n |
| Guide Bar No. 5 | n | n | n | n | n | n | y | n | n | n | n | n |
| Guide Bar No. 4 | n | n | n | n | n | n | y | n | n | n | n | n |
| Guide Bar No. 3 | n | n | n | n | n | n | n | n | n | n | y | n |
| Guide Bar No. 2 | y | n | n | n | n | n | n | n | n | n | n | n |
| Guide Bar No. 1 | n | n | y | y | y | y | n | n | y | y | y | n |

| Guide Bar Chain Notation Details: | | |
|---|---|---|
| Guide Bar No. 1: | 2-0/4-4/4-6/2-2//repeat | Front full thread |
| Guide Bar No. 2: | 4-2/4-4/2-2/2-0//repeat | Left connector |
| Guide Bar No. 3: | 2-2/2-4/0-2/0-0//repeat | Right connector |
| Guide Bar No. 4 Leg: | 4-4/4-2/2-0/2-2//repeat | Bifurcation connector |
| Guide Bar No. 4 Body: | 4-6/2-2/2-0/4-4//repeat | Join Bar No. 1 |
| Guide Bar No. 5 Leg: | 4-6/4-4/2-2/2-4//repeat | Bifurcation connector |
| Guide Bar No. 5 Body: | 4-6/2-2/2-0/4-4//repeat | Join Bar No. 1 |
| Guide Bar No. 6 Leg: | 2-4/2-2/4-4/4-6//repeat | Bifurcation connector |
| Guide Bar No. 6 Body: | 2-2/2-0/4-4/4-6//repeat | Join Bar No. 10 |
| Guide Bar No. 7 Leg: | 2-2/2-0/4-2/4-4//repeat | Bifurcation connector |
| Guide Bar No. 7 Body: | 2-2/2-0/4-4/4-6//repeat | Join Bar No. 10 |
| Guide Bar No. 8: | 0-0/0-2/2-4/2-2//repeat | Right connector |
| Guide Bar No. 9: | 2-0/2-2/4-4/4-2//repeat | Left connector |
| Guide Bar No. 10: | 2-2/4-6/2-2/2-0//repeat | Back full thread |

Graft Processing:

Subsequent to knitting the textile graft, the material was scoured in a basic solution of warm water (e.g., about 65° C. or about 150° F.) and cleaning detergent. It was then rinsed to remove the cleaning agents. The graft was then compacted with methylene chloride at elevated temperatures, for instance about 107° C. or about 224° F., for a short period of time, for instance, three minutes.

Next, the prosthesis was heat-set on stainless steel mandrels to achieve the final desired inside diameter. Typically, the outside diameter of the mandrel was twenty to forty percent oversized to impart, in part, high stretch and low dilation characteristics to the textile graft. Heat setting was accomplished in a convection oven at about 212° C. (about 414° F.) for about 10 minutes.

As a result of the heat setting, the warp yarns were locked in the knitted geometry with a two-needle underlap to build in "spring like" properties that capable of longitudinal expansion. The heat set graft was capable of about 50 to 200 percent longitudinal expansion.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An implantable tubular graft comprising:
a tubular knitted tubular graft comprising a single layer of yarns to define a single layered wall, said yarns being interlaced into stitches in a knit pattern capable of resilient longitudinal elongation and resilient radial contraction of said graft from a quiescent state to an elongated state; wherein said knit pattern is a warp knitted pattern of yarns forming a textile layer having an interior surface and an exterior surface, wherein interior yarns comprise the interior surface and form loops in the longitudinal direction of said graft, and exterior yarns comprise the exterior surface and are diagonally shifted over two or more of the interior yarns in an alternating pattern along a width of said graft before engaging an the interior yarn, wherein single layer of yarns form a graft wall having a thickness of no more than about 0.4 millimeters, and further wherein the elongated length is at least 50 percent by length greater than the quiescent length and the elongated length is no more than about 200 percent by length greater than the quiescent length.

2. The graft of claim 1 wherein said graft has at least 350 stitches per square centimeter.

3. The graft of claim 1 wherein said graft has at least 400 stitches per square centimeter; and
further wherein said graft has no more than about 1,000 stitches per square centimeter.

4. The graft of claim 1 wherein said graft is substantially fluid-tight in the quiescent state.

5. The graft of claim 1 wherein said exterior yarns are diagonally shifted over from three to five of the interior yarns.

6. The graft of claim 1 wherein said diagonally shifted yarns inhibit radial expansion of said graft to diameters greater than the quiescent diameter.

7. The graft of claim 1 wherein said single layer of yarns form a graft wall having a thickness of about at least 0.3 millimeters.

8. The graft of claim 1 wherein said wall comprises a number of tubular legs.

9. The graft of claim 8 wherein said number of tubular legs is two to define a bifurcated graft.

10. The graft of claim 1 further including a tubular layer of PTFE circumferentially disposed and securably attached to said graft.

11. The graft of claim 10 wherein said tubular layer of PTFE is a tubular layer of ePTFE.

12. The graft of claim 1 wherein said yarns are selected from the group consisting of monofilament yarns, multifilament yearns, spun type yarns, flat yarns, twisted yarns, textured yarns, and combinations thereof.

13. The graft of claim 1 wherein said yarns are selected from the group of materials selected from polyesters, polypropylenes, polyethylenes, polyurethanes, polytetrafluoroethylenes or combinations thereof.

14. The graft of claim 13 wherein said polyesters include polyethylene terephthalate polyesters.

15. An implantable tubular graft comprising:
a tubular knitted tubular graft comprising a layer of yarns to define a wall, said yarns being interlaced into stitches in a knit pattern capable of resilient longitudinal elongation and resilient radial contraction of said graft from a quiescent state to an elongated;

wherein said knit pattern is a warp knitted pattern of yarns forming a textile layer having an interior surface and an exterior surface, wherein interior yarns comprise the interior surface and form loops in the longitudinal direction of said graft, and exterior yarns comprise the exterior surface and are diagonally shifted over two or more of the interior yarns in an alternating pattern along a width of said graft before engaging an the interior yarn, wherein said layer of yarns form a graft wall having a thickness of no more than about 0.4 millimeters, and further wherein the longitudinal expansion is at least about 50 percent by length of the length in the quiescent state and the longitudinal expansion is no more than about 200 percent by length of the length in the quiescent state.

16. The graft of claim 15 wherein said yarns are interlaced into a number of stitches from about 400 stitches per square centimeter to about 1,000 stitches per square centimeter to provide compliancy in the quiescent state.

17. The graft of claim 15 wherein said exterior yarns are diagonally shifted over from three to five of the interior yarns.

18. The graft of claim 15 wherein said layer of yarns form a graft wall having a thickness of at least about 0.3 millimeters.

19. The graft of claim 15 wherein said wall comprises a number of tubular legs.

20. The graft of claim 19 wherein said number of tubular legs is two to define a bifurcated graft.

21. The graft of claim 15 wherein said graft has a substantially fluid-tight quiescent state.

22. The graft of claim 15 wherein said yarns are selected from the group consisting of monofilament yarns, multifilament yearns, spun type yarns, flat yarns, twisted yarns, textured yarns, and combinations thereof.

23. The graft of claim 15 wherein said yarns are selected from the group of materials selected from polyesters, polypropylenes, polyethylenes, polyurethanes, polytetrafluoroethylenes or combinations thereof.

24. The graft of claim 23 wherein said polyesters include polyethylene terephthalate polyesters.

25. The graft of claim 15 wherein said pattern has at least about 20 stitches per centimeter in the longitudinal direction of the graft; and
further wherein said pattern has no more than about 50 stitches per centimeter in the longitudinal direction of the graft.

26. An implantable device comprising:
a textile structure having a single layer of yarns to define a tubular wall having a first surface and a second opposed surface, wherein a first yarn comprises the first surface and forms loops in the longitudinal direction of said structure, and a second yarn comprises the second surface and is diagonally shifted over two or more of the first yarns in an alternating pattern along a width of said structure before engaging the first yarn to permit longitudinal expansion of at least about 50 percent by length of the length of said structure.

27. An implantable device comprising:
a textile structure having a single layer of yarns interlaced into stitches in a knit pattern capable of resilient longitudinal expansion from a quiescent state and having at least about 400 stitches per square centimeter and further having no more than about 1,000 stitches per square centimeter to provide compliancy for the structure;
wherein said knit pattern is a warp knitted pattern of yarns forming a textile layer having a first surface and a second opposed surface, wherein a first yarn comprises the first surface and forms loops in the longitudinal direction of said fabric, and a second yarn comprises the second surface and is diagonally shifted over two or more of the first yarns in an alternating pattern along a width of said fabric before engaging the first yarn, and further wherein said textile structure is a tubular graft structure or a medical fabric structure.

28. A knitted medical fabric comprising:
a knitted structure having a single layer of yarns interlaced into stitches in a knit pattern capable of resilient longitudinal expansion from a quiescent state and having at least about 400 stitches per square centimeter and further having no more than about 1,000 stitches per square centimeter to provide compliancy for the structure;
wherein said knit pattern is a warp knitted pattern of yarns forming a textile layer having a first surface and a second opposed surface, wherein a first yarn comprises the first surface and forms loops in the longitudinal direction of said fabric, and a second yarn comprises the second surface and is diagonally shifted over two or more of the first yarns in an alternating pattern along a width of said fabric before engaging a the first yarn.

29. The medical fabric of claim 28 wherein the longitudinal expansion is at least about 50 percent by length of the quiescent length; and
further wherein the longitudinal expansion is no more than about 200 percent by length of the quiescent length.

30. The medical fabric of claim 28 wherein said graft has a substantially fluid-tight quiescent state.

31. The medical fabric of claim 28 wherein said yarns are polyethylene terephthalate polyester textured yarns having a denier of at least 30; and further wherein said polyethylene terephthalate polyester textured yarns have a denier to about 80.

* * * * *